(12) United States Patent
Song (10) Patent No.: US 8,171,820 B2
(45) Date of Patent: May 8, 2012

(54) BIOMETRIC STEERING WHEEL

(75) Inventor: Kidong Song, Gunpo-si (KR)

(73) Assignee: Hyundai Motor Company, Seoul (KR)

( * ) Notice: Subject to any disclaimer, the term of this patent is extended or adjusted under 35 U.S.C. 154(b) by 210 days.

(21) Appl. No.: 12/618,327

(22) Filed: Nov. 13, 2009

(65) Prior Publication Data

US 2011/0048163 A1    Mar. 3, 2011

(30) Foreign Application Priority Data

Sep. 3, 2009    (KR) ........................ 10-2009-0082924

(51) Int. Cl.
  *B62D 1/04*    (2006.01)
  *B62D 1/06*    (2006.01)
  *A61B 5/0404*    (2006.01)
(52) U.S. Cl. ......................................... 74/552; 340/576
(58) Field of Classification Search ................ 74/484 R, 74/552, 558, 558.5; 29/894.1; 600/372, 600/393; 482/8; 200/61.54; 340/575, 576; 219/204; *B62D 1/06*
  See application file for complete search history.

(56) References Cited

U.S. PATENT DOCUMENTS

| | | | | | |
|---|---|---|---|---|---|
| 1,093,441 A | * | 4/1914 | Laurance | ........................ | 74/552 |
| 3,466,644 A | * | 9/1969 | Dean | ............................. | 361/232 |
| 3,485,974 A | * | 12/1969 | Wolf et al. | ................. | 200/61.57 |
| 4,706,072 A | * | 11/1987 | Ikeyama | ........................ | 340/576 |
| 5,453,929 A | * | 9/1995 | Stove | ................................ | 701/1 |
| 5,855,144 A | * | 1/1999 | Parada | ............................ | 74/552 |
| 6,104,296 A | * | 8/2000 | Yasushi et al. | ................ | 340/576 |
| 6,239,707 B1 | * | 5/2001 | Park | ................................ | 340/576 |
| 7,894,887 B2 | * | 2/2011 | Yanai et al. | .................... | 600/509 |
| 2003/0110881 A1 | * | 6/2003 | Lorenz | ............................. | 74/552 |
| 2006/0025698 A1 | * | 2/2006 | Nakagawa et al. | ........... | 600/513 |
| 2007/0244400 A1 | * | 10/2007 | Honda | ........................... | 600/509 |
| 2008/0238695 A1 | * | 10/2008 | Yanai et al. | .................. | 340/576 |

FOREIGN PATENT DOCUMENTS

| | | |
|---|---|---|
| JP | 11-225975 | 8/1999 |
| JP | 2003-148967 A | 5/2003 |
| JP | 2008-237378 A | 10/2006 |
| JP | 2008-237379 A | 10/2006 |
| JP | 2008-301959 A | 12/2008 |
| KR | 10-2007-0028745 A | 3/2007 |
| KR | 10-2007-0093201 A | 9/2007 |

* cited by examiner

*Primary Examiner* — James Pilkington
*Assistant Examiner* — Thomas Diaz
(74) *Attorney, Agent, or Firm* — Morgan, Lewis & Bockius LLP (57) ABSTRACT

A biometric steering wheel, may include sensing members that are disposed along the circumferential direction of the steering wheel and exposed to the outside on a surface of the steering wheel, in at least two sectors of the steering wheel, wherein the sensing members have electric conductivity.

9 Claims, 7 Drawing Sheets

FIG.7 though exemplified by being illustrated and described herein, including, for example,

BIOMETRIC STEERING WHEEL

CROSS-REFERENCE TO RELATED APPLICATIONS

The present application claims priority to Korean Patent Application Number 10-2009-0082924 filed Sep. 3, 2009, the entire contents of which application is incorporated herein for all purposes by this reference.

BACKGROUND OF THE INVENTION

1. Field of the Invention

The present invention relates to a steering wheel of a vehicle, in detail, a biometric steering wheel that can measure biosignals of a driver.

2. Description of Related Art

Vehicles are equipped with a steering wheel that transmits an operational force for controlling the direction of the vehicles and drivers generally continuously operates the steering wheels with hands while driving the vehicles. It is possible to provide new function, which cannot be obtained in the related art, for users, by acquiring and utilizing biosignals, which can be acquired from driver's hands, using a steering wheel.

That is, it is possible to provide service about the present health condition of drivers, by acquiring biosignals from the drivers' hands through a steering wheel and analyzing the biosignals.

Further, other than that, more kinds of services are possible in accordance with development of the technology analyzing biosignals acquired as described above.

It is the most basic and necessary in the above service to stably acquire desired biosignals from drivers without inconveniencing the drivers.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY OF THE INVENTION

Various aspects of the present invention are directed to provide a biometric steering wheel that makes it possible to stably detect and ensure biosignals of a driver, by operating the steering wheel in the same way as the related art, without inconveniencing the driver.

In an aspect of the present invention, a biometric steering wheel, including sensing members that are disposed along the circumferential direction of the steering wheel and exposed to the outside on a surface of the steering wheel, in at least two sectors of the steering wheel, wherein the sensing members have electric conductivity.

The sensing members may be disposed along the exterior circumferential direction of the steering wheel.

The sensing members may include at least two or more sensing members disposed in parallel along the circumferential direction of the steering wheel in each of the at least two sectors, wherein two pairs of sensing members are disposed in two sectors at left and right sides of the steering wheel, respectively, with respect to the forward direction of a vehicle.

A length of the at least two sectors may be longer than half of the entire circumference of the steering wheel.

The biometric steering wheel may include a core forming the structure of the steering wheel, and an insert that is disposed between the core and the sensing members and fixes the sensing members thereto, wherein the sensing members having a U-shape cross section extend along the circumferential direction of the steering wheel, and an opening of the U-shaped cross section of the sensing member is fitted on the insert.

The biometric steering wheel may further include at least a fixing pin that fixes the sensing members to the insert while passing through both the insert and the sensing members fitted on the insert, wherein the at least a fixing pin and the insert are non-conductor.

In another aspect of the present invention, the biometric steering wheel may include at least a clip coupled to the insert by passing therethrough and fixing the insert to the core by enclosing the core therein, and at least a clip-fixing member that allows the at least a clip to enclose the core therein in a closed curve, by fixing both distal ends of the clip to the core, wherein the at least a clip-fixing member includes a bolt that is connected to the core by passing through a portion where the both distal ends of the clip overlap.

The core having a U-shaped cross section may extends along the circumferential direction of the steering wheel, the both distal ends of the clip overlap at an opening of the U-shape cross section of the core, a filler member is inserted in a space between the overlapping portion of the clip and the U-shaped cross section of the core to fill the space, and the bolt is screwed in the filler member through the overlapping portion of the clip.

A body may be formed such that the outer side of the core and the insert is covered by the body and a connecting portion of the U-shaped cross section of the sensing member is exposed to the outside through the body.

Various aspects of the present invention has a simple configuration and structure and makes it possible to stably detect and ensure biosignals of a driver, by operating the steering wheel in the same way as the related art, without inconveniencing the driver.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION OF THE INVENTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Referring to FIGS. 1 to 7, an exemplary embodiment of the present invention includes sensing members 3 that are disposed in at least two sectors of a steering wheel in the circumferential direction of the steering wheel 1 while being exposed to the outside on the surface of the steering wheel.

In an exemplary embodiment of the present invention, sensing members 3 are arranged in pairs of at least two pieces in parallel in the circumferential direction of the steering wheel in the sectors, and made of an electric conductive material, such as metal plate.

Since it is preferable that the sectors where sensing members 3 are disposed are portions that a driver the most frequently touches, in this exemplary embodiment, two pairs of two sensing members 3 are disposed at both left and right sectors of the steering wheel, respectively.

Further, in this exemplary embodiment, sensing members 3 are disposed in the sectors which are longer than half of the entire circumference of steering wheel 1 to increase contact possibility of the driver.

The steering wheel has a core 5 forming the structure and an insert 7 is disposed between core 5 and sensing member 3, such that the pairs of sensing members 3 can be fixed in parallel with each other at a predetermined distance in the circumferential direction of the steering wheel.

Sensing member 3 has a U-shaped cross section and extends in the circumferential direction of the steering wheel and the opening of the U-shaped cross section of sensing member 3 is fitted around insert 7.

Fixing pins 9 pass through both all of sensing members 3 fitted in pairs on insert 7 and insert 7 in order to fix sensing member 3 fitted on insert 7, such that sensing members 3 are fixed to inserts 7.

Insert 7 and fixing pin 9 are made of a non-conductor of electricity, such as plastic, to prevent electric connection between the pairs of sensing members 3, and between sensing members 3 and core 5.

In order to fix inserts 7 with sensing members 3 fixed by fixing pin 9 to core 5, as described above, arc-shaped clips 11 that fix inserts 7 to core 5 by covering core 5 while passing through inserts 7 are used.

That is, both ends of clip 11 is fixed to core 5 by a specific clip-fixing member such that a closed curve covering core 5 by the clip passing through insert is formed.

Although adhesive may be used for the clip-fixing member, in this exemplary embodiment, a fixing bolt 13 that is connected to core 5 through a portion where both ends of clip 11 overlap is used.

Figure 6:
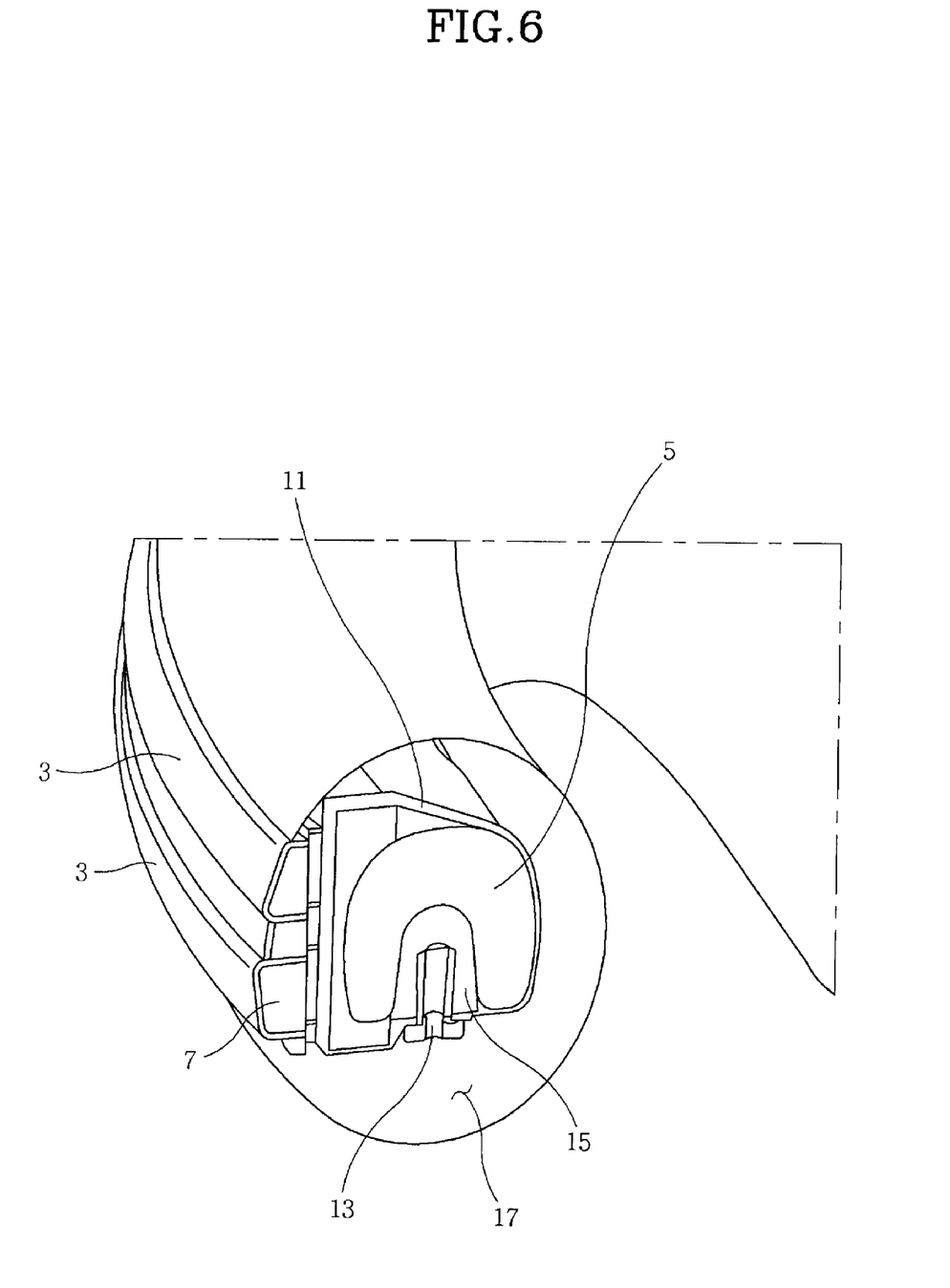
FIG. 6 is a cross-sectional view taken along the line VI-VI of FIG. 4.
Figure 7:
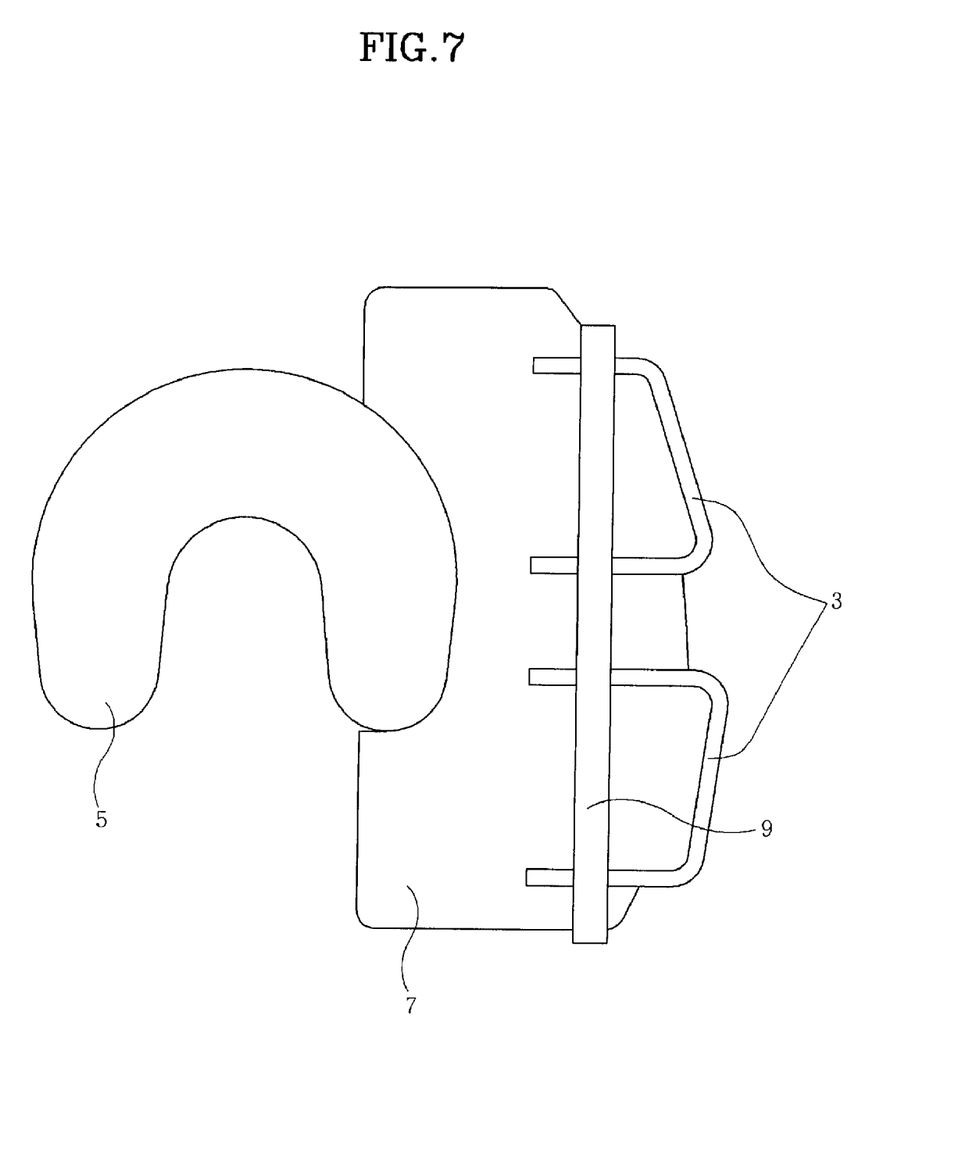
FIG. 7 is a cross-sectional view taken along the line VII-VII of FIG. 4.

Referring to FIG. 6, core 5 extends in the circumferential direction of the steering wheel while having a U-shaped cross section in this exemplary embodiment. Both ends of clip 11 overlap at the opening of the U-shaped cross section of core 5, a filler member 15 is inserted in a space formed between the overlapping portion of clip 11 and core 5 to fill the space, and fixing bolt 13 is screwed in filler member 15 through the overlapping portion of clip 11

Figure 1:
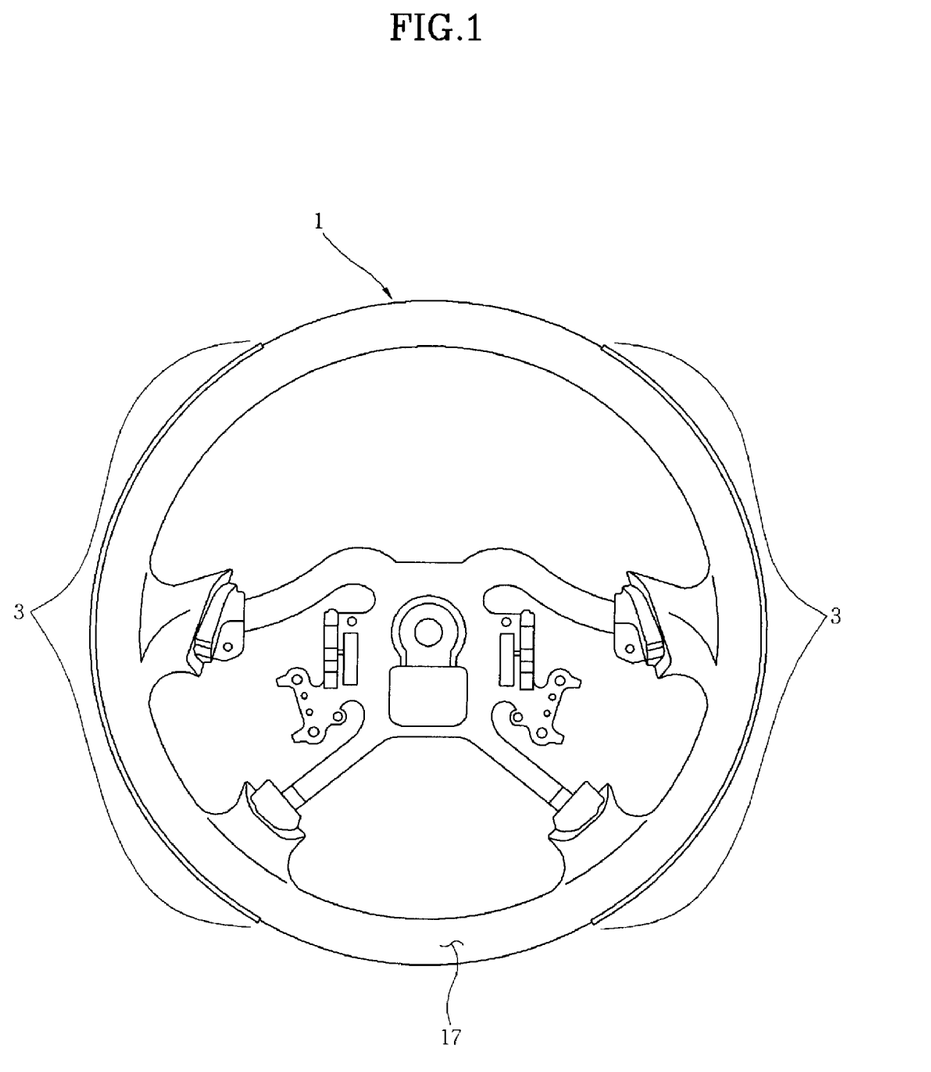
FIG. 1 is a view showing a biometric steering wheel according to an exemplary embodiment of the present invention.
Figure 2:
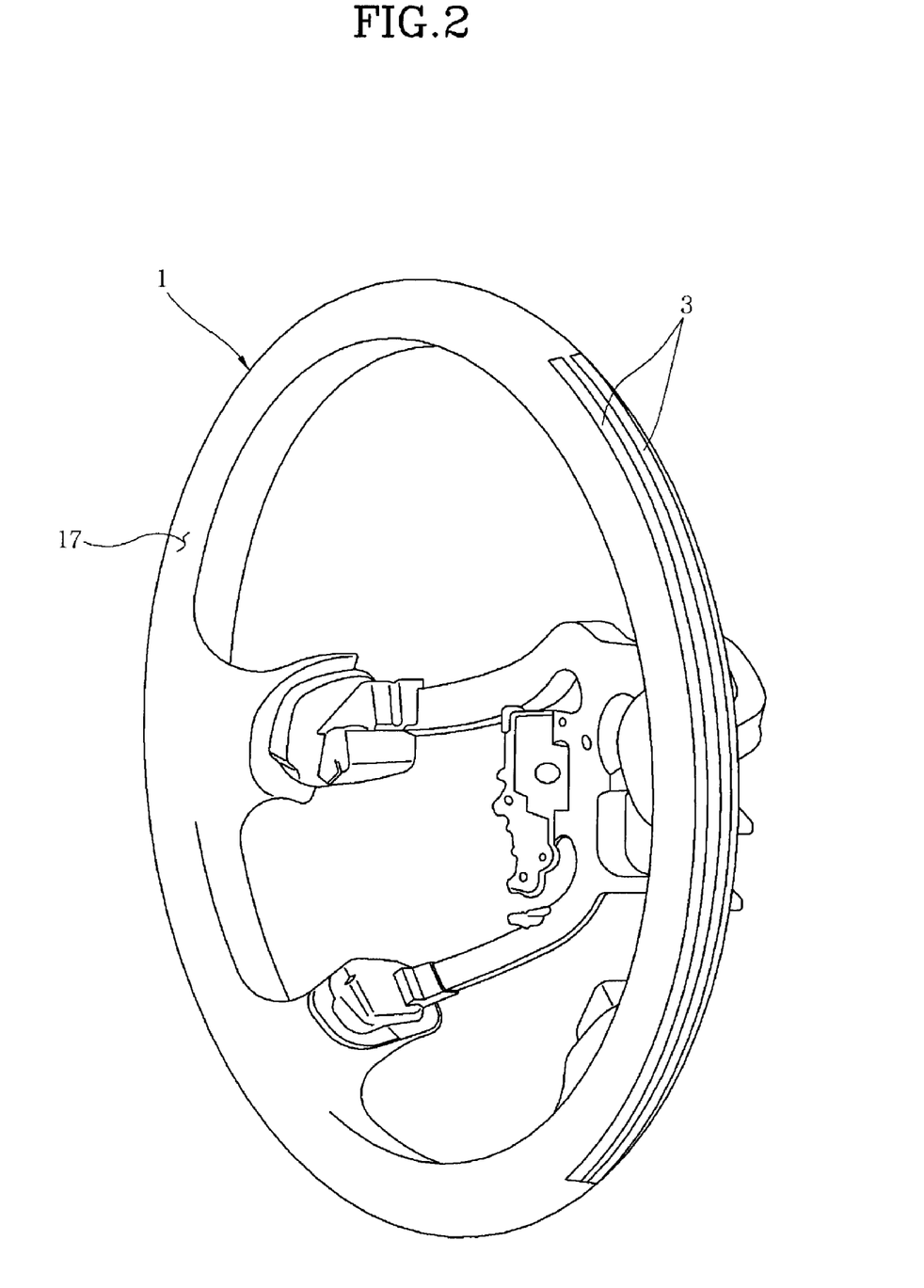
FIG. 2 is a view showing FIG. 1 at another angle.
Figure 3:
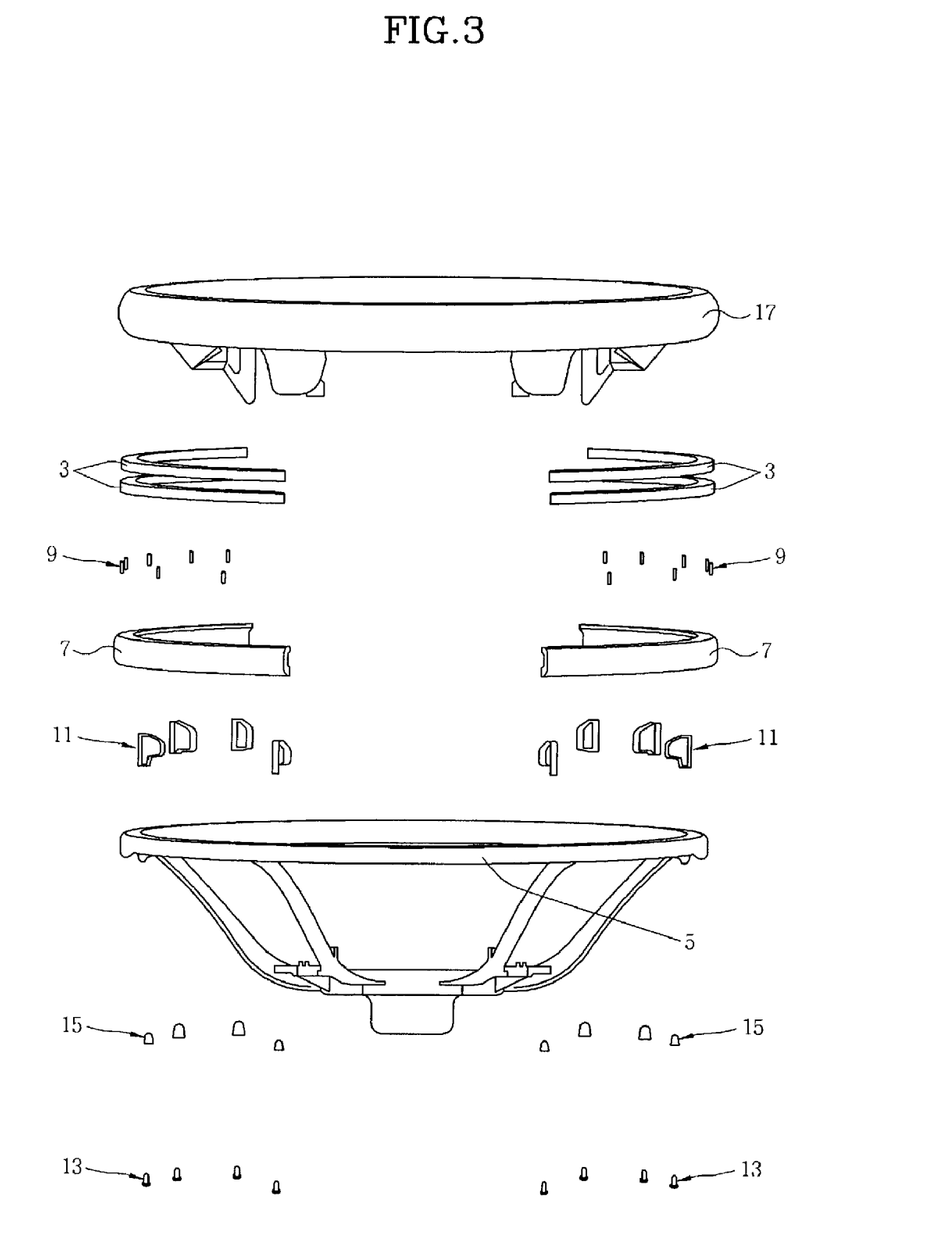
FIG. 3 is an exploded view of the biometric steering wheel of FIG. 1.
Figure 4:
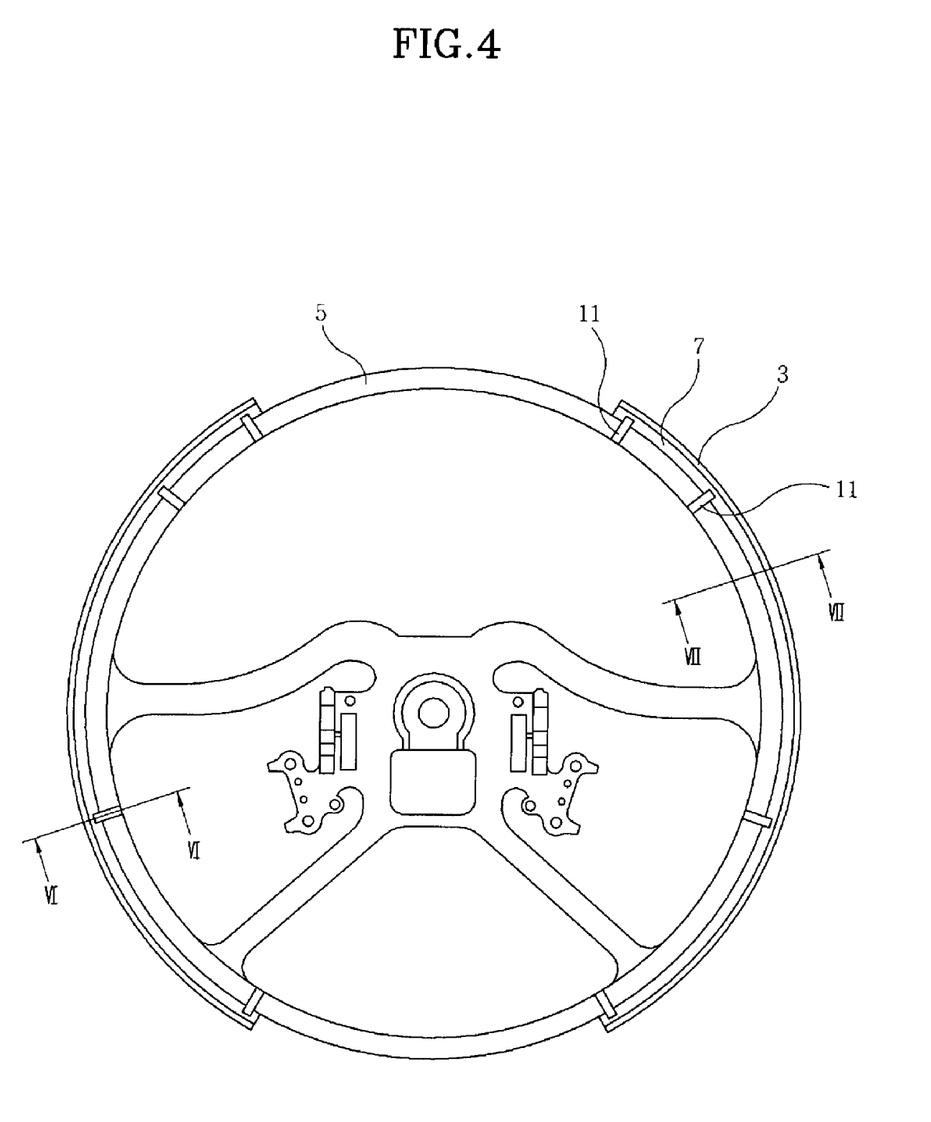
FIG. 4 is a view showing when a core and an insert are combined before a body is formed.
Figure 5:
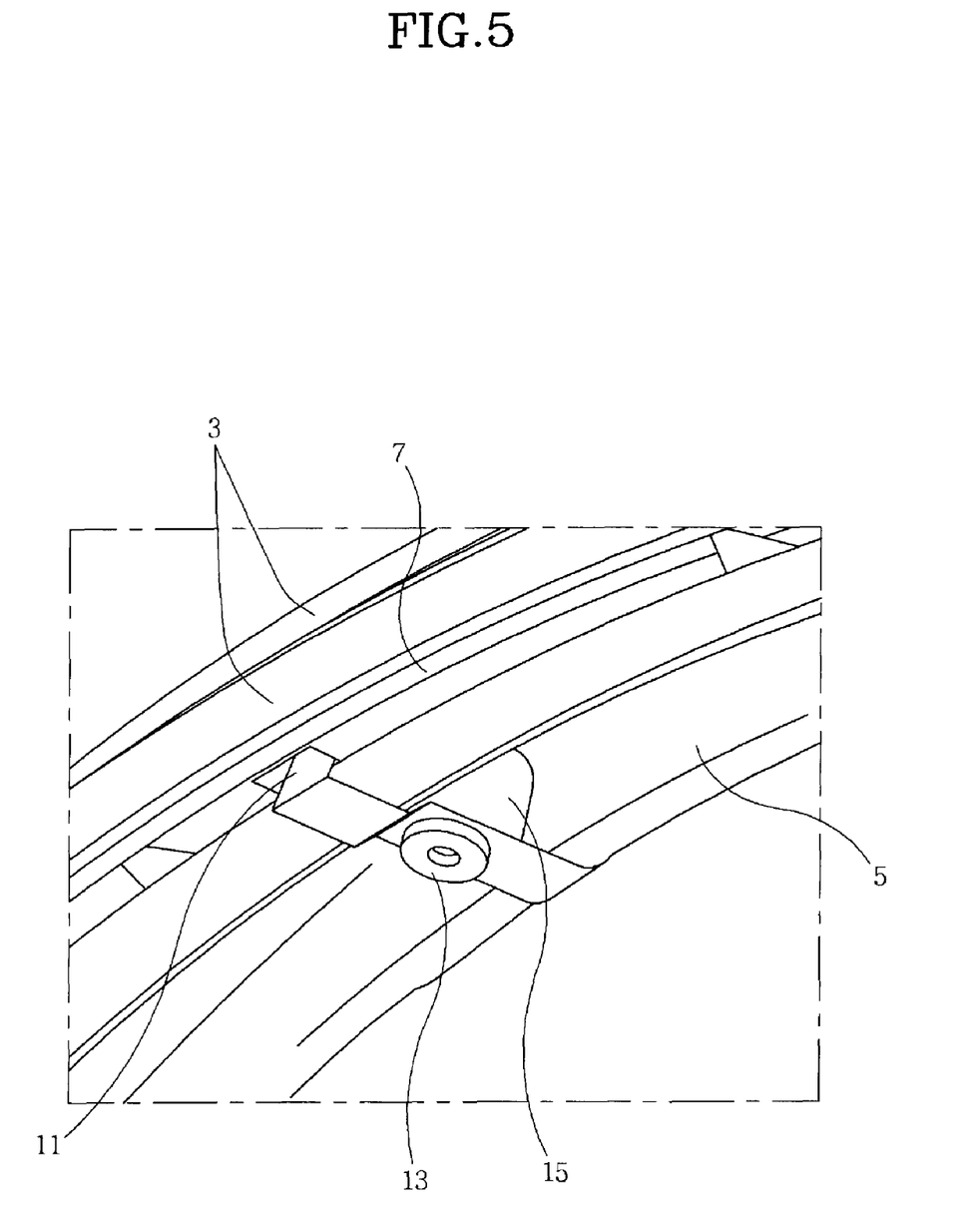
FIG. 5 is a view showing a clip installation portion, seen from the rear of FIG. 4.

Finally, as shown in FIG. 4, the biometric steering wheel according to an exemplary embodiment of the present invention is formed such that only the connecting portions of the U-shaped cross section of sensing member 3 are exposed to the outside while a body 17 covers inserts 7 and core 5, after inserts 7 with sensing members 3 are fixed to core 5 by clips 11, such that it is finished in the shape shown in FIGS. 1 and 2.

For reference, the opening of the U-shaped cross section implies the portion where both upper ends of the U-shape are separated and the connecting portion of the U-shaped cross section implies the joint of the lower portions of the U-shaped cross section.

Sensing members 3 are connected to electric wires inside steering wheel 1 to transmit signals to an electronic device that can process the signals from sensing members 3.

The shape of biometric steering wheel 1 having the above configuration is maintained and supported by core 5 in which only the connecting portions of the U-shaped cross sections of sensing members 3 is exposed outside on the surface of the steering wheel and the other portions are all covered by body 17. Accordingly, sensing members 3 are prevented from separating from steering wheel 1 or deforming by an airbag swelling or shock from a passenger, such that it is possible to stably detect biosignals from the driver's hands.

For convenience in explanation and accurate definition in the appended claims, the terms "left" and "right" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A biometric steering wheel comprising:
sensing members that are disposed along the circumferential direction of the steering wheel and exposed to the outside on a surface of the steering wheel, in at least two sectors of the steering wheel, wherein the sensing members have electric conductivity,
a core forming the structure of the steering wheel;
an insert that is disposed between the core and the sensing members and fixes the sensing members thereto, wherein the sensing members having a U-shape cross section and extend along the circumferential direction of the steering wheel, and an opening of the U-shaped cross section of the sensing member is fitted on the insert; and at least a fixing pin that fixes the sensing members to the insert while passing through both the insert and the sensing members fitted on the insert, wherein the at least a fixing pin and the insert are non-conductor.

2. The biometric steering wheel as defined in claim 1, wherein the sensing members are disposed along the exterior circumferential direction of the steering wheel.

3. The biometric steering wheel as defined in claim 1, wherein the sensing members include at least two or more sensing members disposed in parallel along the circumferential direction of the steering wheel in each of the at least two sectors.

4. The biometric steering wheel as defined in claim 3, wherein two pairs of sensing members are disposed in two sectors at left and right sides of the steering wheel, respectively, with respect to the forward direction of a vehicle.

5. The biometric steering wheel as defined in claim 1, wherein a length of each of the at least two sectors is longer than half of the entire circumference of the steering wheel.

6. The biometric steering wheel as defined in claim 1, further comprising:

at least a clip coupled to the insert by passing therethrough and fixing the insert to the core by enclosing the core therein; and at least a clip-fixing member that allows the at least a clip to enclose the core therein in a closed curve, by fixing both distal ends of the clip to the core.

7. The biometric steering wheel as defined in claim 6, wherein the at least a clip-fixing member includes a bolt that is connected to the core by passing through a portion of the clip where the both distal ends of the clip overlap.

8. The biometric steering wheel as defined in claim 7, wherein the core having a U-shaped cross section extends along the circumferential direction of the steering wheel, the both distal ends of the clip overlap at an opening of the U-shape cross section of the core, a filler member is inserted in a space between the overlapping portion of the clip and the U-shaped cross section of the core to fill the space, and the bolt is screwed in the filler member through the overlapping portion of the clip.

9. The biometric steering wheel as defined in claim 1, wherein a body is formed such that the outer side of the core and the insert is covered by the body and a connecting portion of the U-shaped cross section of the sensing member is exposed to the outside through the body.

\* \* \* \* \*